United States Patent [19]
Weinmann et al.

[11] Patent Number: 6,084,004
[45] Date of Patent: Jul. 4, 2000

[54] COMPOSITIONS WHICH UNDERGO LIGHT-INDUCED CATIONIC CURING AND THEIR USE

[75] Inventors: Wolfgang Weinmann, Herrsching; Gunther Eckhardt, Frieding, both of Germany

[73] Assignee: Espe Dental AG, Seefeld, Germany

[21] Appl. No.: 09/138,281

[22] Filed: Aug. 21, 1998

[30] Foreign Application Priority Data

Aug. 21, 1997 [DE] Germany .............................. 197 36 471

[51] Int. Cl.[7] ...................................................... C08F 2/46
[52] U.S. Cl. ................................. 522/25; 522/31; 522/7; 522/100; 522/168; 522/170
[58] Field of Search .................................. 522/25, 7, 168, 522/100, 170, 31

[56] References Cited

U.S. PATENT DOCUMENTS

| | | | |
|---|---|---|---|
| 4,071,424 | 1/1978 | Dart et al. | 204/159.15 |
| 4,156,035 | 5/1979 | Tsao et al. | 427/44 |
| 4,256,828 | 3/1981 | Smith | 430/280 |
| 4,439,380 | 3/1984 | Michl et al. | 264/16 |
| 4,835,193 | 5/1989 | Hayase et al. | 522/15 |
| 5,086,192 | 2/1992 | Kessel et al. . | |
| 5,144,051 | 9/1992 | Kessel et al. . | |
| 5,321,053 | 6/1994 | Hino et al. | 522/26 |
| 5,401,528 | 3/1995 | Schmidt | 427/2.26 |
| 5,639,802 | 6/1997 | Neckers et al. | 522/25 |
| 5,667,541 | 9/1997 | Klun et al. . | |
| 5,750,590 | 5/1998 | Scheafer et al. | 523/115 |
| 5,856,373 | 1/1999 | Kaisaki et al. | 522/25 |

FOREIGN PATENT DOCUMENTS

| | | |
|---|---|---|
| 0285369 | 10/1988 | European Pat. Off. . |
| 0 330 117 A2 | 8/1989 | European Pat. Off. . |
| 3833437 | 4/1990 | Germany . |
| 2639395 | 3/1991 | Germany . |
| 19534594 | 3/1997 | Germany . |
| 9514716 | 6/1995 | WIPO . |
| 96/13538 | 5/1996 | WIPO . |
| 9613538 | 5/1996 | WIPO . |

OTHER PUBLICATIONS

Chemical Abstracts, "Synthetic High Polymers", vol. 121, 1994, p. 3 (58047).

*Primary Examiner*—James J. Seidleck
*Assistant Examiner*—Sanza L. McClendon
*Attorney, Agent, or Firm*—Birch, Stewart, Kolasch & Birch, LLP

[57] ABSTRACT

The invention relates to compositions which undergo cationic curing with visible light, comprising:
(a) 0.01 to 8 wt. % of at least one diaryliodonium compound,
(b) 0.01 to 8 wt. % of at least one α-dicarbonyl compound,
(c) 10.0 to 99.9 wt. % of at least one compound containing epoxide groups and/or oxetane groups,
(d) 0 to 85 wt. % of modifiers, such as fillers, dyestuffs, pigments, flow improvers, thixotropic agents, polymeric thickeners, additives having an oxidizing action, stabilizers and retardants, characterized in that they additionally comprise
(e) 0.001 to 5 wt. % of at least one aromatic amine.

The compositions have a low intrinsic color, cure with little smell and, after curing, give compositions with very good mechanical properties.

27 Claims, No Drawings

COMPOSITIONS WHICH UNDERGO LIGHT-INDUCED CATIONIC CURING AND THEIR USE

The invention relates to compositions based epoxy resins and/or oxetanes which cure by cationic polymerization during or after irradiation with visible light. The invention particularly relates to compositions which have only a slight intrinsic colour and to their use in dental preparations.

As is known, compositions comprising compounds which contain epoxide and/or oxetane groups can cure cationically. The cationic polymerization is usually triggered by LEWIS or BRÖNSTED acids, it being possible for these acids either to be added to the cationically curable formulation or to be produced by prior chemical and, in particular, photochemical reactions.

A number of so-called photoinitiators which dissociate under the action of light of the wavelength range from 215 to 400 nm to form BRÖNSTED acids are thus known for compositions containing epoxide groups. These initiators include, for example, diazonium compounds (U.S. Pat. No. 3,205,157), sulphonium compounds (U.S. Pat. No. 4,173,476) and iodonium compounds (U.S. Pat. Nos. 4,264,703, 4,394,403). However, for polymerization of cationically curable compositions, it is necessary to use ultraviolet light for the examples mentioned.

Photolabile substances which liberate LEWIS or BRÖNSTED acids when irradiated with visible light and can cause the polymerization of cationically curable formulations are also known. These photoinitiators are in general derivatives of cyclopentadienyl-iron-arene complexes (EP-A-0 094 915, WO 96/03453, EP-A-0 661 324). These photoinitiators have the disadvantage of giving brown to black polymers, which in cases of dental applications leads to aesthetically unsatisfactory results. Furthermore, an intensive smell of isopropylbenzene occurs during the curing, which is undesirable in dental applications.

Initiator systems which render cationic polymerization possible in the visible range are moreover known. However, these comprise coloured sensitizers, for example xanthenes or flourenes, the chromophoric groups of which are retained and colour the polymers (WO-95/14716; Chemical Abstracts, vol. 121, 1994, ref. 58043z), and are therefore not suitable for aesthetically acceptable dental compositions.

According to WO 96/13538, epoxide systems which can be cured in visible light and have an improved depth of hardening and which comprise
a) a cationically polymerizable epoxy resin,
b) a material containing hydroxyl groups,
c) an aryliodonium salt and
d) an alpha-dicarbonyl compound
are described. The alpha-dicarbonyl compound acts as a sensitizer in the visible range, camphorquinone particularly preferably being employed. As is known, camphorquinone dissociates when irradiated with visible light to form free radicals, this reaction having been used for a long time for initiating the curing operation of formulations containing double bonds, and preferably of dental preparations.

Combined initiator systems of camphorquinone and iodonium compounds are furthermore known, but are employed only for polymerization of compositions which contain double bonds or other compositions which cure by means of free radicals, or for polymerization of hybrid monomer mixtures (U.S. Pat. Nos. 5,554,676, 4,828,583).

Although the use of compounds containing hydroxyl groups leads to the reaction acceleration, which is known from many publications, in the cationic polymerization of epoxide compounds, which is initiated by iodonium compounds and has already been described to achieve flexibilized epoxide compositions (U.S. Pat. Nos. 4,256,828; 4,231,951; EP-B-0 119 425; DE-A-4 324 322.3), the use of relatively high concentrations, such as are mentioned in patent examples 1 to 6, 10 to 16, 22, 23, 32 and 33 of WO 96/13538, of low molecular weight compounds containing hydroxyl groups can lead to an incomplete bonding into the polymeric network, with the consequences of poor mechanical properties and high extractable contents.

The object of the invention is to provide compositions which undergo light-induced cationic curing, which have a low intrinsic colour, which cure with little smell and the curing of which leads to compositions with very good mechanical properties, such as high cohesion, high compressive strength and flexural strength, and low extractable contents.

This object is achieved by compositions which undergo light-induced cationic curing and comprise
a) 0.01 to 8 wt. %, preferably 0.1 to 5 wt. %, of at least one diaryliodonium compound or a mixture of diaryliodonium compounds,
b) 0.01 to 8 wt. %, preferably 0.1 to 5 wt. %, of at least one α-dicarbonyl compound,
c) 10.0 to 99.0 wt. % of at least one compound containing epoxide groups and/or oxetane groups,
d) 0 to 85 wt. % of modifiers, such as fillers, dyestuffs, pigments, flow improvers, thixotropic agents, polymeric thickeners, additives having an oxidizing action, stabilizers and retardants,
characterized in that they additionally comprise
e) 0.001 to 5 wt. %, preferably 0.01 to 3 wt. %, of at least one aromatic amine.

It is surprising that the amines employed for constituent e) have an accelerating action on the light-induced cationic polymerization. It is thus described in the prior art (DE-A-195 34 594, WO 96/13538) that amines have a retarding or even inhibiting effect on polymerization. It is furthermore completely surprising that a very small addition, for example 0.001 wt. %, already has an accelerating action in the polymerizing composition.

The diaryliodonium compounds of constituent a) have the following structure:

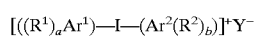

$Ar^1$ and $Ar^2$ independently of one another can be different substituted or unsubstituted, fused or non-fused aromatic systems having 4 to 20 C atoms, such as, for example, phenyl, tolyl, cumyl, anisyl, chlorophenyl, nitrophenyl, naphthyl, thienyl, furanyl and pyrazolyl, wherein $R^1$ and $R^2$ are identical or different and independently of one another denote an H atom, an aliphatic radical having 1 to 19, preferably 1 to 9 C atoms, it being possible for one or more C atoms to be replaced by O, C=—O(C=O)—, F, Cl, Br, $SiR^3_3$ and/or $NR^3_2$ wherein $R^3$ is an aliphatic radical having 1 to 7 C atoms, in which one or more C atoms can be replaced by O, C=O and/or —O(C=O)—, and a and b independently of one another can be 1–5. The aromatics $Ar^1$ and $Ar^2$ can be bonded to one another via $R^1$ and/or $R^2$.

The counter-anion $Y^-$ is an anion of low nucleophilicity of the following structure

wherein K is an element of main group III, V or VII, such as, for example, B, Al, P, Sb, As or I, and x can assume numerical values from 1 to 4, L independently of one another denotes aromatic, aliphatic, araliphatic or cycloaliphatic radicals having 1–25 C atoms, in which one or more C atoms can be replaced by F, Cl, Br or I, and y can assume numerical values from 0 to 6. Preferred radicals L are pentafluorophenyl, tetrafluorophenyl, trifluorophenyl, fluorophenyl, phenyl, 4-trifluoromethyl phenyl, 3,5-bis (trifluoromethyl)phenyl, 2,4,6-tris(trifluoromethyl)-phenyl, fluorine and iodine. Particularly preferred counter-ions $Y^-$ are $PF_6^-$, $SbF_6^-$ and $B(C_6F_5)_4^-$. Further diaryliodonium compounds are also described, for example, in U.S. Pat. No. 4,246,703.

Particularly suitable diaryliodonium compounds are:
diphenyliodonium tetrafluoroborate
diphenyliodonium hexafluorophosphate
diphenyliodonium hexafluoroantimonate
diphenyliodonium tetrakis(pentafluorophenyl)borate
bis-(4-methylphenyl) iodonium hexafluorophosphate
bis-(4-methylphenyl)iodonium hexafluoroantimonate
bis-(4-methylphenyl)iodonium tetrakis(pentafluorophenyl) borate
phenyl-4-methylphenyliodonium hexafluorophosphate
phenyl-4-methylphenyliodonium hexafluoroantimonate
phenyl-4-methylphenyliodonium tetrakis (pentafluorophenyl)borate
phenyl-4-methoxyphenyliodonium hexafluoroantimonate
phenyl-4-methoxyphenyliodonium tetrakis (pentafluorophenyl)borate
phenyl-3-nitrophenyliodonium hexafluorophenylantimonate
phenyl-3-nitrophenyliodonium tetrakis (pentafluorophenyl) borate
bis(4-tert-butylphenyl)iodonium hexafluoroantimonate
bis (4-tert-butylphenyl)iodonium tetrakis (pentafluorophenyl) borate
phenyl 4-diphenyliodonium hexafluoroantimonate
dinaphthyliodonium hexafluorophosphate
dinaphthyliodonium hexafluoroantimonate
dinaphthyliodonium tetrakis(pentafluorophenyl)borate
bis (4-dodecylphenyl) iodonium hexafluoroantimonate
bis(4-dodecylphenyl)iodonium tetrakis(pentafluorophenyl) borate
4-methylphenyl-4-isopropylphenyliodonium hexafluoroantimonate
4-methylphenyl-4-isopropylphenyliodonium tetrakis (pentafluorophenyl)borate α-Dicarbonyl compounds of constituent b) are to be understood as compounds of the following structure:

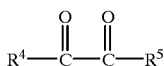

wherein $R^4$ and $R^5$ are identical or different and can be substituted or unsubstituted and aliphatic or aromatic. $R^4$ and $R^5$ together can form ring structures, which are unsubstituted or substituted by aliphatic, cycloaliphatic, aromatic, heteroaromatic or fused aromatic radicals. Preferred α-dicarbonyl compounds are camphorquinone, benzil, 2,3-butanedione and 3,3,6,6-tetramethylcyclohexanedione, camphorquinone being particularly preferred.

Cationically curable compounds of constituent c) are to be understood as aliphatic or aromatic epoxides (type 1), cycloaliphatic epoxides (type 2) or oxetanes (type 3) having the following structures:

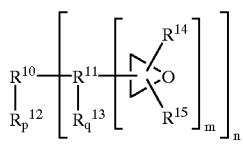
Type 1

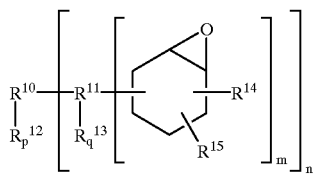
Type 2

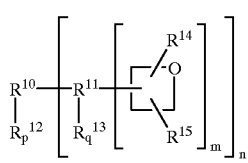
Type 3

The symbols denote:
$R^{10}$ an aliphatic, cycloaliphatic or aromatic radical having 0 to 22, preferably 0 to 18 C atoms or a combination of these radicals, it being possible for one or more C atoms to be replaced by O, C=O, —O(C=O)—, $SiR_3$ and/or $NR_2$, and wherein R is an aliphatic radical having 1 to 7 C atoms, it being possible for one or more C atoms to be replaced by O, C=O and/or O(C=O)—,
$R^{11}$ an aliphatic, cycloaliphatic or aromatic radical having 1 to 18, preferably 1 to 15 C atoms or a combination of these radicals, it being possible for one or more C atoms to be replaced by O, C=O, —O(C=O)—, $SiR_3$ and/or $NR_2$, wherein R is an aliphatic radical having 1 to 7 C atoms, in which one or more C atoms can be replaced by O, C=O and/or —O(C=O)—,
$R^{12}$, $R^{13}$, $R^{14}$, $R^{15}$ independently of one another an H atom or an aliphatic radical having 1 to 9, preferably 1 to 7 C atoms, it being possible for one or more C atoms to be replaced by O, C=O, —O(C=O)—, $SiR_3$ and/or $NR_2$, wherein R is an aliphatic radical having 1 to 7 C atoms, in which one or more C atoms can be replaced by O, C=O and/or —O(C=O)—,
n 2 to 7, preferably 2 to 5, in particular 2 to 4,
m 1 to 10, preferably 1 to 7, in particular 1 to 5,
p 1 to 5, preferably 1 to 4, in particular 1 or 2,
q 1 to 5, preferably 1 to 4, in particular 1 or 2

Particularly suitable epoxides and oxetanes according to components c) are
tetrakis(2,1-ethanediyl-3,4-epoxycyclohexyl)-1,3,5,7-tetramethylcyclotetrasiloxane,
1,10-decanediylbis (oxymethylene)bis (3-ethyloxetane),
1,3,5,7,9-pentakis(2,1-ethanediyl-3,4-epoxycyclohexyl)-1,3,5,7,9-pentamethylcyclopentasiloxane,
vinylcyclohexene oxide,
vinylcyclohexene dioxide,
3,4-epoxy-6-methylcyclohexylmethyl 3,4-epoxy-6-methylcyclohexenecarboxylate,
bis(2,3-epoxycyclopentyl) ether,
3,4-epoxy-6-methylcyclohexylmethyl adipate,
3,4-epoxycyclohexyl-5,5-spiro-3,4-epoxycyclohexanemetadioxane,
1,4-butanediyl-bisoxymethylenebis(3-ethyloxetane),
3,4-epoxycyclohexylmethyl 3,4-epoxycyclohexanecarboxylate, 1,1,3,3-tetramethyl-1,3-bis(2,1-ethanediyl-3,4-epoxycyclohexyl)disiloxane,
bis-(3,4-epoxycyclohexylmethyl) adipate Fillers of constituent d) can be the customary dental fillers, for example quartz, ground, optionally X-ray-opaque or reactive glasses, splinter polymers, sparingly soluble fluorides, such as $CaF_2$, $YF_3$ (EP-B-0 238 025), silica gels and pyrogenic silicic acid or granules thereof.

It is also possible for the compositions to comprise one or more water-soluble inorganic complex fluorides of the general formula $A_nMF_m$, wherein A denotes a mono-or polyvalent cation, M denotes a metal of main or sub-group II, III, IV or V, n denotes an integer from 1 to 3 and m denotes an integer from 3 to 6 (DE-A-4 445 266), as fluoride-donating constituents.

For better incorporation into the polymer matrix, it may be advantageous to hydrophobize the filler and, if appropriate, the X-ray-opaque additives, such as $YF_3$. Customary hydrophobizing agents are silanes, for example glycidyloxypropyltrimethoxysilane. The maximum particle size of the inorganic fillers is preferably 20 μm, in particular 12 μm. Fillers having an average particle size of less than 7 μm are especially preferably employed.

The additives of constituent d) which have an oxidizing action can be organic or inorganic solids or liquids. These additives accelerate the initiation and increase the degree of polymerization. Suitable additives having an oxidizing action are hydroperoxides, such as cumene hydroperoxide, dialkyl peroxides, such as di-tert-butyl peroxide, diaryl peroxides, such as dibenzoyl peroxide, peresters, such as tert-butyl perbenzoate or tert-butyl isononanoate, or inorganic oxidizing agents, such as potassium persulphate or sodium perborate, particularly preferably cumene hydroperoxide or potassium persulphate.

Aromatic amines of constituent e) are to be understood as compounds which have the following structure:

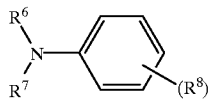

wherein $R^6$, $R^7$ and $R^8$ are identical or different and independently of one another denote an H atom, an aliphatic, aromatic or araliphatic radical having 1 to 19, preferably 1 to 7 C atoms, it being possible for one or more C atoms to be replaced by O, C=O, —O(C=O)—, $SiR^9_3$ and/or $NR^9_2$, wherein $R^9$ is an aliphatic radical having 1 to 7 C atoms, in which one or more C atoms can be replaced by O, C=O and/or —O(C=O)—, and z can assume numerical values from 1 to 5. $R^6$ and $R^7$ or/and $R^6$ and $R^8$ together can form ring structures which are unsubstituted or substituted by aliphatic, cycloaliphatic, aromatic, heteroaromatic or fused aromatic radicals.

Preferred amines are dimethylaniline, diethylaniline, ethyl 4-dimethyl-aminobenzoate, 2-butoxyethyl 4-dimethylaminobenzoate, 2-ethylhexyl 4-dimethylaminobenzoate, 4-dimethylaminobenzaldehyde and its derivatives, such benzaldoximes, azomethines, benzylideneaniline, hydrobenzamide, benzoins, benzils, hydrobenzoins and benzoic acid benzyl esters.

The compositions according to the invention are prepared by mixing the individual constituents together. The sequence of the addition is not critical. Preferably, the compound containing epoxide groups and/or oxetane groups is initially introduced into the mixing vessel and the diaryliodonium compound, the α-dicarbonyl compound and the aromatic amine are stirred into this. The filler and the other modifying agents are then kneaded in.

The compositions according to the invention are suitable for light-induced cationic polymerization on the basis of compounds containing epoxide groups and/or oxetane groups. The initiator system is suitable for curing compositions having a filler content. The compositions offer a particular advantage in dental use. The polymerizable formulations have surprisingly short curing times, it being possible for these curing times to be adjusted very accurately by the nature and concentration of additional activators, for example additives having an oxidizing action.

The compositions according to the invention are suitable for gluing, embedding and coating substrates and for dental compositions.

A very substantial advantage of the compositions according to the invention is the exceptionally good aesthetic impression of the cured compositions. The polymers can be formulated with the colour of teeth and as a result are particularly suitable for dental use. Due to the high transparency of the polymers, an exceptional depth of curing is achieved.

The invention is explained further with the aid of the following examples:

EXAMPLES

The cationically curable one-component compositions with no filler content according to examples 1 to 13 are prepared by mixing the compounds described in table 1. These compositions are the resin matrix for compositions with a filler content (composites) prepared therefrom, according to examples 14 to 20 (table 2).

TABLE 1

Constituents of the cationically curable one-component compositions with no filler content

| | | Examples (composition in wt. %) | | | | | | | | | | | | |
|---|---|---|---|---|---|---|---|---|---|---|---|---|---|---|
| Constituent | Compound | 1 | 2 | 3 | 4 | 5 | 6 | 7 | 8 | 9 | 10 | 11 | 12 | 13 |
| a) | Bis-(4-dodecylphenyl)iodonium-hexafluoroantimonate | 1.05 | | 0.6 | 2.0 | 1.0 | | 2.0 | | 1.2 | | | 2.1 | 2.0 |
| a) | 4-Methylphenyl-4-isopropylphenyl-iodonium tetrakis(pentafluorophenyl)borate | | 1.4 | | | 1.2 | 2.0 | | 2.0 | 1.0 | 2.1 | 2.1 | | |
| b) | Camphorquinone | 1.05 | 1.4 | 0.6 | 0.9 | 0.5 | 0.4 | 0.4 | 0.8 | 0.6 | 0.85 | 0.895 | 0.89 | 1.0 |
| e) | Ethyl 4-dimethylaminobenzoate | 0.9 | | 0.6 | | 0.3 | 0.1 | 0.2 | | 0.2 | 0.05 | 0.005 | 0.005 | |
| e) | 2-Butoxyethyl 4-dimethylaminobenzoate | | 0.1 | | 0.4 | | | | 0.2 | 0.3 | | | 0.005 | 0.3 |

TABLE 1-continued

Constituents of the cationically curable one-component compositions with no filler content

| Constituent | Compound | Examples (composition in wt. %) | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| c) | 3,4-Epoxycyclohexylmethyl 3,4-epoxycyclohexanecarboxylate | 80.0 | 50.0 | 48.0 | | | | 97.0 | 48.5 | | 48.5 | 30.0 | 48.5 | 48.7 |
| c) | Bis-(3,4-epoxycyclohexylmethyl) adipate | 17.0 | | | 33.0 | | 48.7 | | | 48.3 | | 48.5 | 30.0 | |
| c) | 1,3,5,7-Tetrakis-(2,1-ethanediyl-3,4-epoxycyclohexyl)-1,3,5,7-tetramethylcyclotetrasiloxane | | 46.0 | 49.0 | 64.0 | | 48.7 | | | 48.4 | 48.5 | 27.0 | 48.5 | 48 |
| c) | 3,3'-(1,10-Decanediylbis(oxy-methylene))bis(3-ethoxylate) | | | | | 97.0 | | | 48.5 | | | | | |
| d) | Cumene hydroperoxide/80% in cumene | | 1.1 | 1.2 | | | | | | | | | | |
| d) | $K_2S_2O_8$ | | | | | | | | | 0.9 | | | | |
| d) | + tert-butyl perbenzoate | | | | | | | | | | | | | 0.5 |

All the compositions according to examples 1 to 13 cured within 20 seconds when irradiated with a lamp (light apparatus Elipar II, ESPE Dental-Medizin GmbH and Co. KG Germany) which generates visible light in the wavelength range from 400 to 500 nm. The resulting polymers were transparent and had high strengths.

The composite composition characterized in table 2, according to examples 14 to 20, cured within 40 seconds when irradiated with the lamp described.

TABLE 2

Composition of the cationically curable one-component formulations with a filler content

| Example No. | Composition with no filler content | Fillers | | |
|---|---|---|---|---|
| | Composition corresponding to example no. | Silbond[a] 800 EST wt. % | Quartz[b] wt. % | Splinter polymer[c] wt. % |
| 14 | 6 | 30 | | 70 |
| 15 | 7 | 22 | 78 | |
| 16 | 11 | 40 | | 60 |
| 17 | 12 | 27 | 73 | |
| 18 | 12 | 25 | | 75 |
| 19 | 12 | 40 | | 60 |
| 20 | 13 | 29 | 71 | |

[a]Ground quartz flour, silanized, Quarzwerke Frechen
[b]Quartz, average particle size 0.9 μm, was silanized with 5% glycidyloxypropyltrimethoxysilane
[c]The splinter polymer was obtained by grinding and sieving the cured composition according to example 7.

The resulting polymers were colourless to the colour of teeth.

Table 3 contains the results of the determination of essential properties which were achieved using the composite compositions according to examples 14 to 20.

TABLE 3

Properties of the cured compositions of examples 14 to 20

| Example | Flexural strength ISO 4049 | Compressive strength |
|---|---|---|
| 14 | 110 MPa | 381 MPa |
| 15 | 131 MPa | 410 MPa |
| 16 | 95 MPa | 352 MPa |

TABLE 3-continued

Properties of the cured compositions of examples 14 to 20

| Example | Flexural strength ISO 4049 | Compressive strength |
|---|---|---|
| 17 | 99 MPa | 361 MPa |
| 18 | 122 MPa | 395 MPa |
| 19 | 75 MPa | 297 MPa |
| 20 | 113 MPa | 356 MPa |

The examples demonstrate that cured compositions which, because of the only slight intrinsic colour and the very good mechanical properties, are outstandingly suitable for dental applications, and in particular for filling materials and fixing cements, can be achieved with the compositions according to the invention.

What is claimed is:

1. Composition which undergoes cationic curing with visible light, comprising
    (a) 0.01 to 8 wt. % of at least one diaryliodonium compound,
    (b) 0.01 to 8 wt. % of at least one α-dicarbonyl compound,
    (c) 10.0 to 99.9 wt. % of at least one compound containing epoxide groups and/or oxetane groups,
    (d) 0 to 85 wt. % of modifiers, such as fillers, dyestuffs, pigments, flow improvers, thixotropic agents, polymeric thickeners, additives having an oxidizing action, stabilizers and retardants,
characterized in that it additionally comprises
    (e) 0.001 to 5 wt. % of at least one aromatic amine.

2. Composition according to claim 1, characterized in that it comprises the constituents
    (a) in an amount of 0.1 to 5 wt. %
    (b) in an amount of 0.1 to 5 wt. % and
    (e) in an amount of 0.01 to 3 wt. %.

3. Compositions according to claim 1, characterized in that the diaryliodonium compounds of constituent (a) have the following structure:

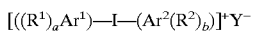

wherein the symbols denote:
    $Ar^1$, $Ar^2$ independently of one another different, substituted or unsubstituted, fused or non-fused aromatic systems having 4 to 20 C atoms, preferably phenyl, tolyl, cumyl, anisyl, chlorophenyl, nitrophenyl, naphthyl, thienyl, furanyl and pyrazolyl, $R^1$, $R^2$ independently of one another an H atom, an aliphatic radical having 1 to 19, preferably 1 to 9 C atoms, it being possible for one or more C atoms to be replaced by O, C=O, —O(C=O)—, F, Cl, Br, $SiR^3{}_3$ and/or $NR^3{}_2$, wherein $R^3$ is an aliphatic radical having 1 to 7 C atoms, in which one or more C atoms can be replaced by O, C=O and/or —O(C=O)—, wherein the aromatics $Ar^1$ and $Ar^2$ can be bonded to one another via $R^1$ and/or $R^2$, a and b independently of one another an integer from 1 to 5 and $Y^-$ an anion of little nucleophilicity of the formula $K_xL_y$ wherein the symbols denote:

K an element of main group III, V or VII, preferably B, Al, P, Sb, As or I x a number from 1 to 4

L independently of one another aromatic, aliphatic, araliphatic or cycloaliphatic radicals having 1–25 C atoms, in which one or more C atoms can be replaced by F, Cl, Br or I, and y a number from 0 to 6.

4. Composition according to claim 3, characterized in that $Y^-$ is $PF_6^-$, $SbF_6^-$ or $B(C_6F_5)_4{}^-$.

5. Composition according to claims 1, characterized in that the α-dicarbonyl compounds of constituent (b) have the following structure:

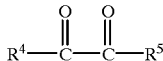

in which $R^4$ and $R^5$ independently of one another can be substituted or unsubstituted and aliphatic or aromatic and $R^4$ and $R^5$ together can form ring structures which are unsubstituted or substituted by aliphatic, cycloaliphatic, aromatic, heteroaromatic or fused aromatic radicals.

6. Composition according to claim 5, characterized in that it comprises, as constituent (b), camphorquinone, benzil, 2,3-butanedione and/or 3,3,6,6-tetramethylcyclohexanedione, preferably camphorquinone.

7. Composition according to claim 1, characterized in that the aromatic amines of constituent (e) have the following structure:

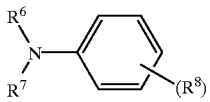

in which $R^6$, $R^7$ and $R^8$ independently of one another denote an H atom, an aliphatic, aromatic or araliphatic radical having 1 to 19, preferably 1 to 7 C atoms, it being possible for one or more C atoms to be replaced by O, C=O, —O(C=O)—, $SiR^9{}_3$ and/or $NR^9{}_2$, and $R^9$ is an aliphatic radical having 1 to 7 C atoms, in which one or more C atoms can be replaced by O, C=O and/or O(C=O), and z can assume numerical values from 1 to 5 and $R^6$ and $R^7$ or/and $R^6$ and $R^8$ together can form ring structures which can be unsubstituted or substituted by aliphatic, cycloaliphatic, aromatic, heteroaromatic or fused aromatic radicals.

8. Composition according to claim 7, characterized in that it comprises, as constituent (c), dimethylaniline, diethylaniline, ethyl 4-dimethyl-aminobenzoate, 2-butoxyethyl 4-dimethylaminobenzoate, 2-ethylhexyl 4-dimethylaminobenzoate, 4-dimethylaminobenzaldehyde, benzaldoximes, azomethines, benzylideneaniline, hydrobenzamide, benzoins, benzils, hydrobenzoins and/or benzoic acid benzyl esters, preferably ethyl 4-dimethyl-aminobenzoate, 2-butoxyethyl 4-dimethylaminobenzoate or 2-ethylhexyl 4-dimethylaminobenzoate.

9. Composition according to claim 1, characterized in that the compounds of constituent (c) containing epoxide groups and/or oxetane groups have the following structure:

Type 1

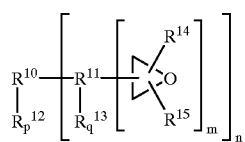

Type 2

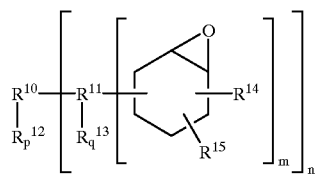

Type 3

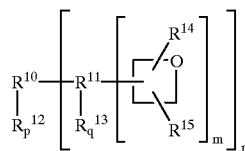

wherein the symbols denote:

$R^{10}$ an aliphatic, cycloaliphatic or aromatic radical having 0 to 22, preferably 0 to 18 C atoms or a combination of these radicals, it being possible for one or more C atoms to be replaced by O, C=O, —O(C=O)—, $SiR_3$ and/or $NR_2$, and wherein R is an aliphatic radical having 1 to 7 C atoms, it being possible for one or more C atoms to be replaced by O, C=O and/or —O(C=O)—, $R^{11}$ an aliphatic, cycloaliphatic or aromatic radical having 1 to 18, preferably 1 to 15 C atoms or a combination of these radicals, it being possible for one or more C atoms to be replaced by O, C=O, —O(C=O)—, $SiR_3$ and/or $NR_2$, wherein R is an aliphatic radical having 1 to 7 C atoms, in which one or more C atoms can be replaced by O, C=O and/or —O(C=O)—, $R^{12}$, $R^{13}$, $R^{14}$, $R^{15}$ independently of one another an H atom or an aliphatic radical having 1 to 9, preferably 1 to 7 C atoms, it being possible for one or more C atoms to be replaced by O, C=O, —O(C=O)—, $SiR_3$ and/or $NR_2$, wherein R is an aliphatic radical having 1 to 7 C atoms, in which one or more C atoms can be replaced by O, C=O and/or —O(C=O)—, n 2 to 7, m 1 to 10, p 1 to 5, q 1 to 5.

10. Composition according to claim 9, characterized in that it comprises, as component (c), 1,3,5,7-tetrakis-(2,1- ethanediyl-3,4-epoxycyclohexyl)-1,3,5,7-tetramethylcyclotetrasiloxane, 1,10-decanediylbis(oxymethylene)bis(3-ethyloxetane), 1,3,5,7,9-pentakis(2,1-ethanediyl-3,4-epoxycyclohexyl) -1,3,5,7,9-pentamethylcyclopentasiloxane, Vinylcyclohexene oxide, vinylcyclohexene dioxide, 3,4-epoxy-6-methylcyclohexylmethyl 3,4-epoxy-6-methylcyclohexanecarboxylate, bis(2,3-epoxycyclopentyl) ether, 3,4-epoxy-6-methylcyclohexylmethyl) adipate, 3,4epoxycyclohexyl-5,5-spiro-3,4-epoxy(cyclohexanemetadioxane), 1,4-butanediyl-bis(oxymethylene)-bis-(3-ethyloxetane), 3,4-epoxycyclohexylmethyl 3,4-epoxycyclohexanecarboxylate, 1,1,3,3-tetramethyl-1,3-bis(2,1-ethanediyl-3,4-epoxycyclohexyl)disiloxane and/or bis-(3,4-epoxycyclohexylmethyl) adipate.

11. Composition according to claim 1, characterized in that it comprises, as the additives of constituent (d) having an oxidizing action, cumene hydroperoxide, di-tert-butyl peroxide, diaryl peroxides, dibenzoyl peroxide, tert-butyl perbenzoate, tert-butyl isononanoate, potassium persulphate and/or sodium perborate.

12. Composition according to claim 1, characterized in that it comprises, as fillers of constituent (d), quartz, ground, optionally X-ray-opaque or reactive glasses, splinter polymers, sparingly soluble fluorides, silica gels and/or pyrogenic silicic acid or granules thereof.

13. The composition according to claim 1, wherein the composition is not cured by means of free radicals.

14. Composition which undergoes cationic curing with visible light, comprising
(a) 0.01 to 8 wt. % of at least one diaryliodonium compound having the following structure:

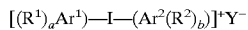

wherein the symbols denote:
$Ar^1$, $Ar^2$ independently of one another different, substituted or unsubstituted, fused or non-fused aromatic systems having 4 to 20 C atoms, preferably phenyl, tolyl, cumyl, anisyl, chlorophenyl, nitrophenyl, naphthyl, thienyl, furanyl and pyrazolyl,
$R^1$, $R^2$ independently of one another an H atom, an aliphatic radical having 1 to 19, preferably 1 to 9 C atoms, it being possible for one or more C atoms to be replaced by O, C=O, —O(C=0)—, F, Cl, Br, $SiR^3_3$ and/or $NR^3_2$, wherein $R^3$ is an aliphatic radical having 1 to 7 C atoms, in which one or more C atoms can be replaced by O, C=O and/or —O(C=O)—, wherein the aromatics $Ar^1$ and $Ar^2$ can be bonded to one another via $R^1$ and/or $R^2$,
a and b independently of one another an integer from 1 to 5 and $Y^-=B(C_6F_5)_4^-$,
(b) 0.01 to 8 wt. % of at least one α-dicarbonyl compound,
(c) 10.0 to 99.9 wt. % of at least one compound containing epoxide groups and/or oxetane groups,
(d) 0 to 85 wt. % of modifiers, such as fillers, dyestuffs, pigments, flow improvers, thixotropic agents, polymeric thickeners, additives having an oxidizing action, stabilizers and retardants, characterized in that it additionally comprises
(e) 0.001 to 5 wt. % of at least one aromatic amine having the following structure:

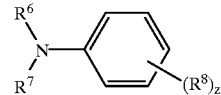

in which $R^6$, $R^7$ and $R^8$ independently of one another denote an H atom, an aliphatic, aromatic or araliphatic radical having 1 to 19 C atoms, it being possible for one or more C atoms to be replaced by O, C=O, —O(C=O)—, $SiR^9_3$ and/or $NR^9_2$, and $R^9$ is an aliphatic radical having 1 to 7 C atoms, in which one or more C atoms can be replaced by O, C=O and/or O(C=O), and z can assume numerical values from 1 to 5 and $R^6$ and $R^7$ and/or $R^6$ and $R^8$ together can form ring structures which can be unsubstituted or substituted by aliphatic cycloaliphatic, aromatic, heteroaromatic or fused aromatic radicals.

15. The composition according to claim 14, wherein $R^6$, $R^7$ and $R^8$ independently of one another denote H atom, an aliphatic, aromatic or araliphatic radical having 1 to 7 C atoms.

16. The composition according to claim 9, wherein n is 2 to 5, m is 1 to 7, p is 1 to 4 and q is 1 to 4.

17. The composition according to claim 9, wherein n is 2 to 4, m is 1 to 5, p is 1 or 2 and q is 1 or 2.

18. The composition according to claim 12, wherein the sparingly soluble fluorides are $CaF_2$ or $YF_3$.

19. The method of gluing, embedding or coating a substrate, comprising contacting a substrate with the composition of claim 1.

20. A dental filling material comprising the composition according to claim 1.

21. A bonding material comprising the composition of claim 1.

22. A filling cement comprising the composition according to claim 1.

23. A fixing cement comprising the composition of claim 1.

24. A plastic for a prostheses comprising the composition according to claim 1.

25. A veneer material comprising the composition according to claim 1.

26. A sealing material comprising the composition according to claim 1.

27. Artificial teeth comprising the composition according to claim 1.

* * * * *